(12) United States Patent
Kimura et al.

(10) Patent No.: US 6,326,628 B1
(45) Date of Patent: Dec. 4, 2001

(54) IMAGE READING APPARATUS

(75) Inventors: Toshihito Kimura; Yukinori Nishioka, both of Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/299,601

(22) Filed: Apr. 27, 1999

(30) Foreign Application Priority Data

Apr. 30, 1998 (JP) .................................................. 10-120654

(51) Int. Cl.⁷ ...................................................... F21V 9/16
(52) U.S. Cl. ...................... 250/458.1; 250/584; 250/585; 250/586
(58) Field of Search .................................... 250/584, 585, 250/586, 458.1

(56) References Cited

U.S. PATENT DOCUMENTS

| | | | |
|---|---|---|---|
| 4,339,469 | * 7/1982 | McDonie et al. ................... | 427/10 |
| 5,141,312 | * 8/1992 | Thompson et al. .................. | 356/218 |
| 5,213,673 | * 5/1993 | Fujimiya et al. .................... | 204/612 |
| 5,665,962 | * 9/1997 | Kimura ................................ | 250/226 |
| 5,900,640 | * 5/1999 | Ogura ................................... | 250/583 |
| 6,023,071 | * 2/2000 | Ogura et al. ......................... | 250/586 |
| 6,043,506 | * 3/2000 | Heffelfinger et al. ............... | 250/584 |
| 6,130,440 | * 10/2000 | Ogura ................................... | 250/586 |

OTHER PUBLICATIONS

WH Turner, "Photoluminescence of color filter glasses", Mar. 1973, Applied Optics 12:480–486.*

* cited by examiner

Primary Examiner—Seungsook Ham
Assistant Examiner—Shun Lee
(74) Attorney, Agent, or Firm—Sughrue, Mion, Zinn, Macpeak & Seas PLLC

(57) ABSTRACT

An image reading apparatus comprises at least one laser stimulating ray source for emitting a laser beam and a light detector for photoelectrically detecting fluorescent light released from an image carrier upon an excitation by the laser beam. The light detector can detect light having wavelength shorter than 700 nm with high sensitivity. The apparatus further comprises a filter provided in front of the light detector that is made of a material to able cut light having wavelength of the laser stimulating ray and emits a fluorescent light having a peak wavelength equal to or longer than 700 nm upon excitation by the laser stimulating ray. According to the thus-constituted image reading apparatus, it is possible to read fluorescent images with high sensitivity.

19 Claims, 6 Drawing Sheets

IMAGE READING APPARATUS

BACKGROUND OF THE INVENTION

1. Field of the Invention

The present invention relates to an image reading apparatus and, particularly, to such an apparatus which can read a fluorescence image with high sensitivity.

2. Description of the Prior Art

A fluorescence detecting system labeling a specimen with a fluorescent substance and reading a fluorescence image, is known. According to this system, it is possible to study a genetic sequence, the expression level of a gene and the metabolism, absorption, excretion path and state of a substance introduced into a test mouse and to effect the separation or identification of protein or the estimation of the molecular weight or properties of protein or the like by the steps of labeling a specimen using the fluorescent substance, irradiating the specimen with radiation, exciting the fluorescent substance contained in the specimen and detecting the released fluorescent light. For example, this system can perform a process including the steps of electrophoresing a plurality of DNA fragments on a gel support after a fluorescent dye was added to a solution containing a plurality of DNA fragments to be electrophoresed or distributing a plurality of DNA fragments on a gel support containing fluorescent dye or dipping a gel support on which a plurality of DNA fragments have been electrophoresed in a solution containing fluorescent dye, thereby labeling the electrophoresed DNA fragments, exciting the fluorescent dye by a stimulating ray to cause it to release a fluorescent light, detecting the released fluorescent light to produce an image and detecting the distribution of the DNA fragments on the gel support. This system also performs a process including the steps of electrophoresing a plurality of DNA fragments on a gel support, denaturing the DNA fragments, transferring at least a part of the denatured DNA fragments onto a transfer support such as nitrocellulose support by the Southern-blotting method, hybridizing a probe prepared by labeling target DNA and DNA or RNA complementary thereto with the denatured DNA fragments, thereby selectively labeling only DNA fragments complementary to the probe DNA or probe RNA, exciting the fluorescent dye by a stimulating ray to cause it to release a fluorescent light, detecting the fluorescent light to produce an image and detecting the distribution of the target DNA fragments on the transfer support. This system can further perform a process including the steps of preparing a DNA probe complementary to DNA containing a target gene labeled by a labeling substance, hybridizing it with DNA on a transfer support, combining an enzyme with complementary DNA labeled by a labeling substance, causing the enzyme to contact a fluorescent substance, transforming the fluorescent substrate to a fluorescent substance having a fluorescent light release property, exciting the thus produced fluorescent substance by a stimulating ray to release fluorescent light, detecting the fluorescent light to produce an image and detecting the distribution of the target DNA fragment on the transfer support. This fluorescent detecting system is advantageous in that a genetic sequence or the like can be easily detected without using a radioactive substance.

The image reading apparatus for reading the fluorescent image carried on the image carrier is constructed so as to scan the image carrier with the stimulating ray to stimulate the fluorescent substance in the carrier and to photoelectrically detect the fluorescent light emitted from the fluorescent substance by a light detector such as a photomultiplier. In order to improve the sensitivity of the detection, a color glass filter is provided in front of the light detector to cut light having the same wavelength as the stimulating ray and transmit light having longer wavelength than that of the stimulating ray, However, the color glass filter tends to emit flourescent light upon irradiation by the stimulating ray. As it is unavoidable that the stimulating light reflected in the apparatus stimulates the color glass filter, the flourescent light emitted from the color filter is photoelectrically detected by the light detector and degrades the sensitivity in image reading.

SUMMARY OF THE INVENTION

It is therefore an object of the present invention to provide an image reading apparatus which can be used in a fluorescence detecting system and can read the fluorescent image with high sensitivity.

The above and other objects of the present invention can be accomplished by an image reading apparatus comprising at least one laser stimulating ray source for emitting a laser beam, a light detector for photoelectrically detecting fluorescent light released from an image carrier upon excitation by the laser beam, the light detector being able to detect light having a wavelength shorter than 700 nm with high sensitivity, filter means provided in front of the light detector and made of a material able to cut light having the wavelength of the laser stimulating ray and that emits fluorescent light having a peak wavelength equal to or longer than 700 nm upon excitation by the laser stimulating ray.

In a preferred aspect of the present invention the peak wavelength of the fluorescent light emitted from the filter means is longer than the wavelength of the stimulating ray by at least 80 nm.

In another preferred aspect of the present invention, the light detector comprises a photomultiplier containing bialkali material and detects the light having a wavelength between 200 nm and 700 nm with high sensitivity.

In a further aspect of the present invention, the photomultiplier contains a bialkali material based on the compound $K_2CsSb$ prepared by activation with oxygen and cesium.

In a further aspect of the present invention, the at least one laser stimulating ray source is a laser stimulating ray source for emitting a laser beam having a wavelength of 633 nm or 635 nm.

In a further aspect of the present invention, the at least one laser stimulating ray source is a laser stimulating ray source for emitting a laser beam having a wavelength between 530 nm and 540 nm.

In a further aspect of the present invention, the at least one laser stimulating ray source is a laser stimulating ray source for emitting a laser beam having a wavelength between 470 nm and 480 nm.

The above and other objects of the present invention can also be accomplished by an image reading apparatus comprising laser beam source means for emitting a laser beam, laser scanning means for scanning an image carrier carrying a fluorescent image thereon with the laser beam emitted from the laser beam source means, a light detector for photoelectrically detecting fluorescent light released from the image carrier upon excitation by the laser beam, the light detector being able to detect light having a wavelength shorter than 700 nm with high sensitivity, filter means provided in front of the light detector for cutting the light having the wavelength of the laser beam and made of a material that emits a fluorescent light having a peak wavelength equal to or longer than 700 nm upon excitation by the laser stimulating ray.

In a preferred aspect of the present invention, the peak wavelength of the fluorescent light emitted from the filter means is longer than the wavelength of the laser beam by at least 80 nm.

In another aspect of the present invention, the light detector comprises a photomultiplier containing bialkali material and detects light having a wavelength between 200 nm and 700 nm with high sensitivity.

In a further aspect of the present invention, the photomultiplier contains a bialkali material based on the compound $K_2CsSb$ prepared by activation with oxygen and cesium.

In a further aspect of the present invention, the at least one laser stimulating ray source is a laser beam source for emitting a laser beam having a wavelength of 633 nm or 635 nm.

In a further aspect of the present invention, the laser beam source is a laser stimulating ray source for emitting a laser beam having a wavelength between 530 nm and 540 nm.

In a further aspect of the present invention, the laser beam source is a laser stimulating ray source for emitting a laser beam having a wavelength between 470 nm and 480 nm.

In a further aspect of the present invention, the laser beam source means includes a plurality of laser beam sources which emit a plurality of laser beams having different wavelengths from each other, and wherein the filter means includes a plurality of filters, each of which is made of a material cutting one of the laser beams and emitting a fluorescent light having a peak wavelength equal to or longer than 700 nm by the excitation of one of the laser beams.

In a further aspect of the present invention, the peak wavelength of the fluorescent light is longer than the wavelength of the laser beam by at least 80 nm.

In a further aspect of the present invention, the laser beam source is a laser stimulating ray source for emitting a laser beam having a wavelength of 633 nm or 635 nm.

In a further aspect of the present invention, the laser beam source is a laser stimulating ray source for emitting a laser beam having a wavelength between 530 nm and 540 nm.

In a further aspect of the present invention, the laser beam source is a laser stimulating ray source for emitting a laser beam having a wavelength between 470 nm and 480 nm.

As termed with respect to the present invention, the phrase "the image carrier carries an image of a fluorescent substance" includes the case where the image carrier carries an image of a specimen labeled with a labeling substance and the case where the image carrier carries an image of a fluorescent substance obtained by combining an enzyme with a specimen labeled with a labeling substance, causing the enzyme to contact a fluorescent substrate and transforming the fluorescent substrate to a fluorescent substance.

In the present invention, the fluorescent dye employed for labeling the specimen to form an image to be carried in an image carrier and read by stimulating it using a laser beam having a wavelength between 470 nm and 480 nm may be any type of fluorescent dye insofar as it can be stimulated by a laser beam having a wavelength between 470 nm and 480 nm. However, preferably employed fluorescent substances stimulable by a laser beam having a wavelength between 470 nm and 480 nm include Fluorescein (C.I. No. 45350), Fluorescein-X indicated by the structural formula (1) shown below, YOYO-1 indicated by the structural formula (2), TOTO-1 indicated by the structural formula (3), YO-PRO-1 indicated by the structural formula (4), Cy-3 (registered trademark) indicated by the structural formula (5), Nile Red indicated by the structural formula (6), BCECF indicated by the structural formula (7), Rhodamine 6G (C.I. No. 45160), Acridine Orange (C.I. No. 46005), SYBR Green ($C_2H_6OS$), Quantum Red, R-Phycoerythrin, Red 613, Red 670, Fluor X, FAM, AttoPhos, Bodipy phosphatidylcholine, SNAFL, Calcium Green, Fura Red, Fluo 3, AllPro, NBD phosphoethanolamine and the like.

In the present invention, the fluorescent substance employed for labeling a specimen to form an image to be carried in an image carrier and read by stimulating it using a laser beam having a wavelength of 633 nm or 635 nm may be any type of fluorescent dye insofar as it can be stimulated by a laser beam having a wavelength of 633 nm or 635 nm. However, preferably employed fluorescent substances stimulable by a laser beam having a wavelength of 633 nm or 635 nm include Cy-5 (registered trademark) indicated by the structural formula (8), Allphycocyanin and the like.

Moreover, in the present invention, the fluorescent substance employed for labeling a specimen to form an image to be carried in an image carrier and read by stimulating it using a laser beam having a wavelength between 530 nm and 540 nm may be any type of fluorescent dye insofar as it can be stimulated by a laser beam having a wavelength between 530 nm and 540 nm. However, preferably employed fluorescent substances stimulable by a laser beam having a wavelength between 530 nm and 540 nm include Cy-3 (registered trademark) indicated by the structural formula (5), Rhodamine 6G (C.I. No. 45160), Rhodamine B (C.I. No.45170), Ethidium Bromide indicated by the structural formula (9), Texas Red indicated by the structural formula (10), Propidium Iodide indicated by the structural formula (11), POPO-3 indicated by the structural formula (12), Red 613, Red 670, Carboxyrhodamine (R6G), R-Phycoeryhthrin, Quantum Red, JOE, HEX, Ethidium homodimer, Lissamine Rhodamine B peptide and the like.

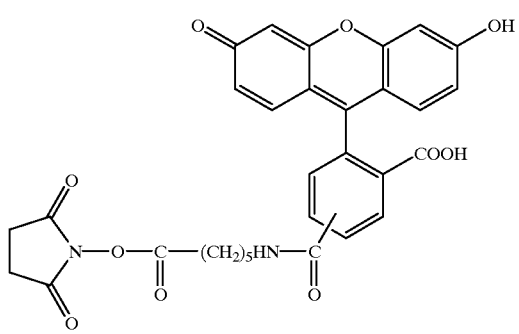

Formula (1)

Flourescein-X

Formula (2)
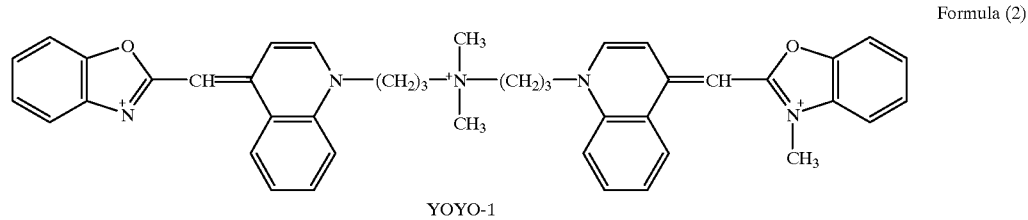
YOYO-1
Formula (3)
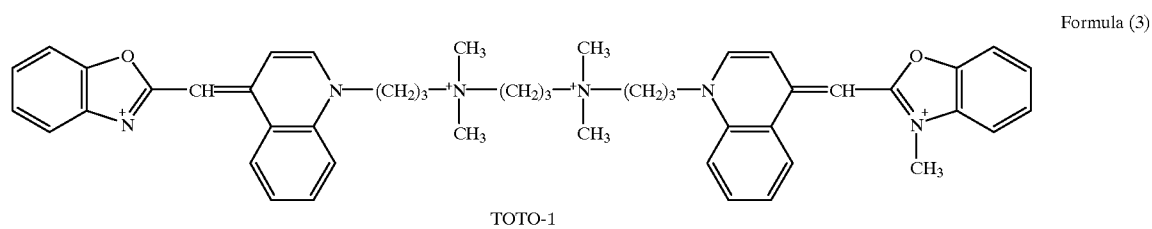
TOTO-1
Formula (4)
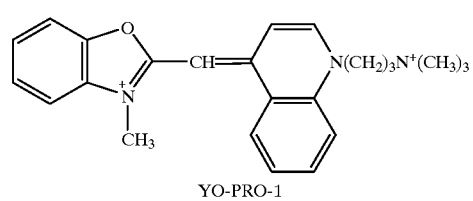
YO-PRO-1
Formula (5)
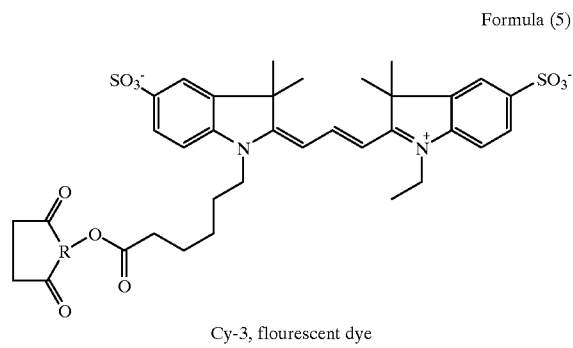
Cy-3, flourescent dye
Formula (6)
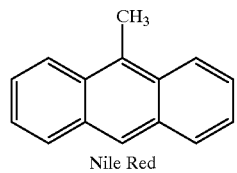
Nile Red Formula (7)
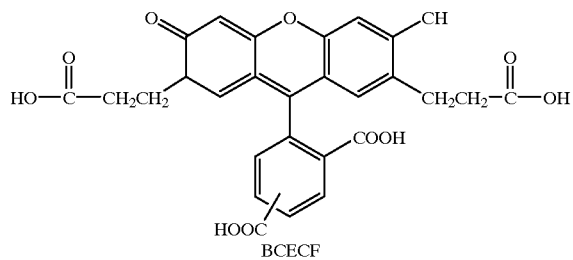
BCECF
Formula (8)
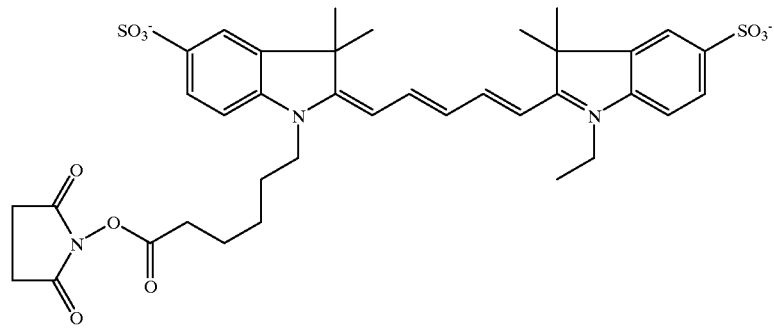
Cy-5, flourescent dye
Formula (9)
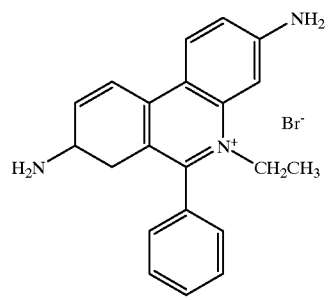
Ethidium Bromide
Formula (10)
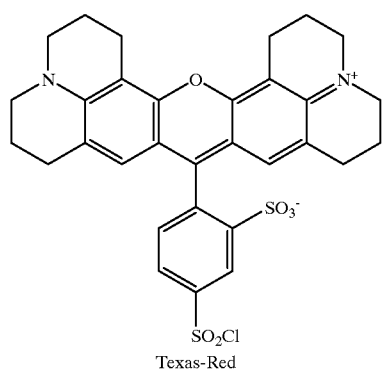
Texas-Red Formula (11)

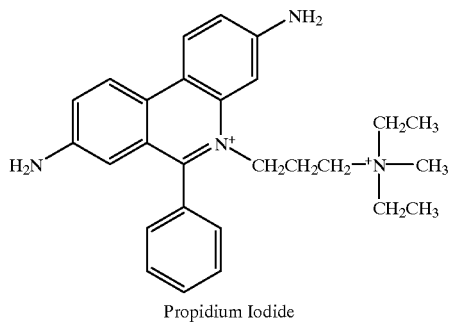

Propidium Iodide

Formula (12)

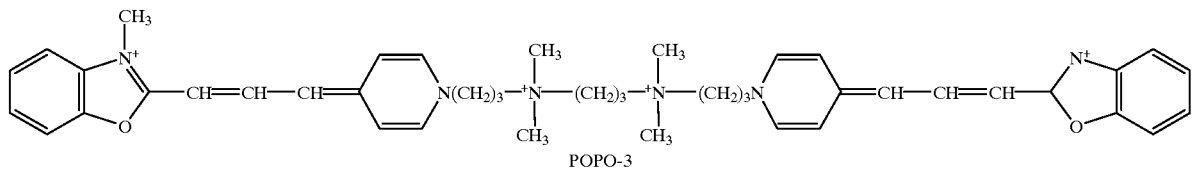

POPO-3

DETAILED DESCRIPTION OF THE PREFERRED EMBODIMENTS

Figure 1:
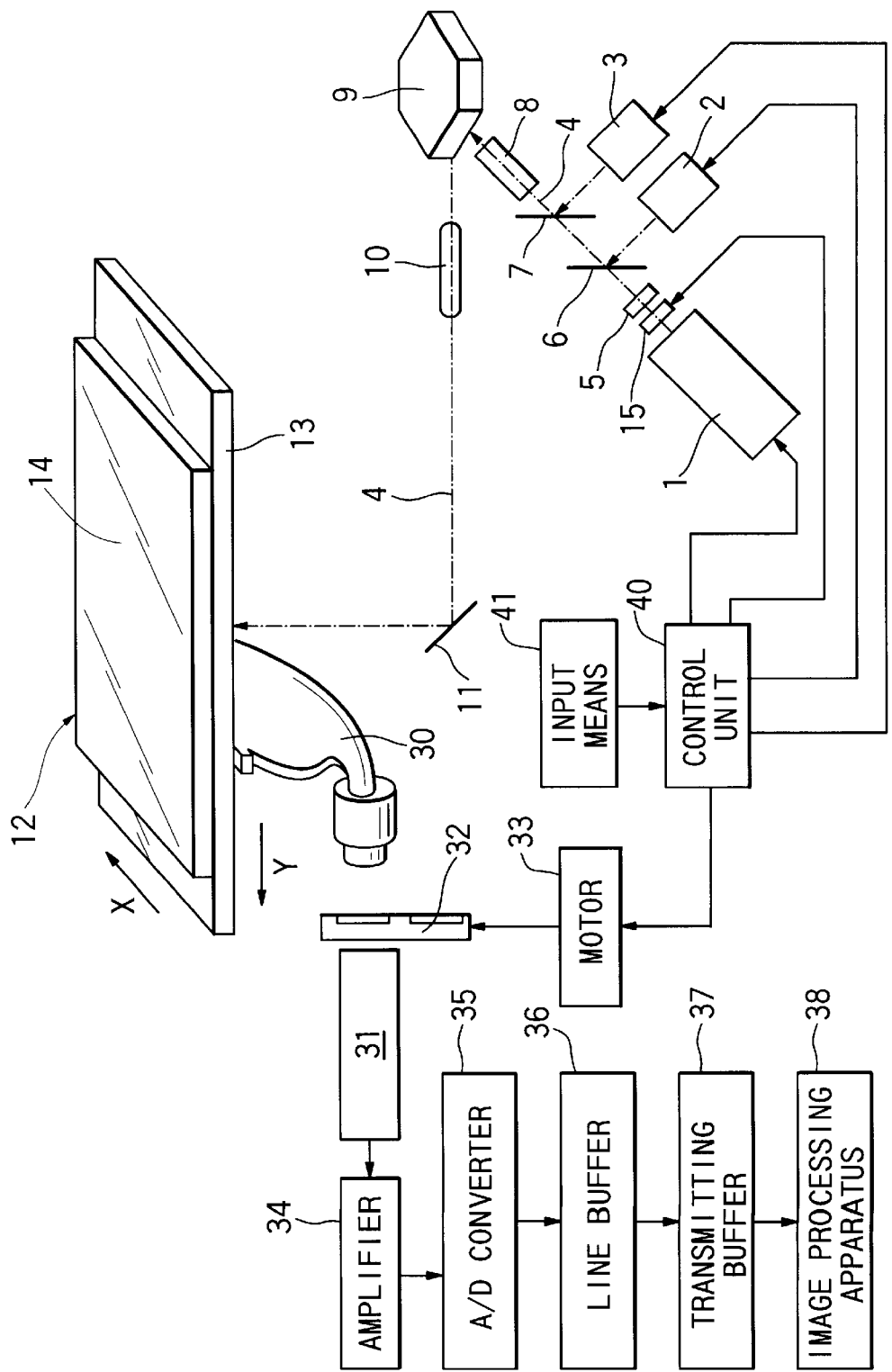
FIG. 1 is a schematic diagram showing an image reading apparatus which is a first embodiment of the present invention.

Referring to FIG. 1, an image reading apparatus of a first embodiment of the present invention includes a first laser stimulating ray source 1 for emitting a laser beam having a wavelength of 633 nm, a second laser stimulating ray source 2 for emitting a laser beam having a wavelength of 532 nm and a third laser stimulating ray source 3 for emitting a laser beam having a wavelength of 473 nm. In this embodiment, the first laser stimulating ray source 1 is constituted by a He—Ne laser beam source and the second laser stimulating ray source 2 and the third laser stimulating ray source 3 are constituted by a second harmonic generation elements.

Laser beam 4 emitted from the first laser stimulating source 1 passes through a filter 5 after passing through a light modulator 15 when it is turned on, thereby cutting light in a wavelength region corresponding to a wavelength region of stimulated emission released from a stimulable phosphor sheet in response to the stimulation by the laser beam 4 having a wavelength of 633 nm. A first dichroic mirror 6 for transmitting light having a wavelength of 633 nm but reflecting light having a wavelength of 532 nm and a second dichroic mirror 7 for transmitting light having a wavelength equal to and longer than 532 nm but reflecting light having a wavelength of 473 nm, are provided in the optical path of the laser beam 4 emitted from the first laser stimulating ray source 1. The laser beam 4 emitted from the first laser stimulating ray source 1 and transmitted through the filter 5 passes through the first dichroic mirror 6 and the second dichroic mirror 7. The laser beam 4 emitted from the second laser stimulating ray source 2 is reflected by the first dichroic mirror 6, thereby changing its direction by 90 degrees, and passes through the second dichroic mirror 7. The laser beam 4 emitted from the third laser stimulating ray source 3 is reflected by the second dichroic mirror 7, thereby changing its direction by 90 degrees. The laser beam 4 emitted from the selected one of the first laser stimulating ray source 1, the second laser stimulating ray source 2 and the third laser stimulating ray source 3 then enters a beam expander 8. The beam diameter of the laser beam 4 is accurately adjusted by the beam expander 8 and impinges on a polygon mirror 9. The laser beam 4 deflected by the polygon mirror 9 passes through an fθ lens 10 and is reflected by a reflecting mirror 11, thereby entering an image carrier unit 12. The fθ lens 10 ensures that the image carrier unit 12 is always scanned with the laser beam 4 at a uniform beam speed when it is scanned with the laser beam 4 in a direction indicated by X, namely, the main scanning direction.

The image recording apparatus according to this embodiment is constituted so as to be able to read out an image of fluorescent dye recorded in a gel support, a transfer support or the like, and a radiation image, an autoradiographic image, a radiographic diffraction image or an electron microscopic image of an object recorded in a stimulable phosphor layer formed on a stimulable phosphor sheet. In FIG. 1, the fluorescent image carrier unit 12 includes a glass plate 13 and a transfer support 14 placed on the glass plate 13 and in which an electrophoresis image of denatured DNA labeled with fluorescent dye is recorded.

The electrophoresis image of denatured DNA labeled with fluorescent dye is recorded in the transfer support 14, for example, in the following manner. First, a plurality of DNA fragments containing a specific gene are separated and distributed on a gel support medium by means of electrophoresis and are denatured by alkali processing to form single-stranded DNA. Then, according to the known Southern Blotting method, the gel support and a transfer support 14 are stacked to transfer at least a part of the denatured DNA fragments onto the transfer support 14 and the transferred DNA fragments are fixed on the transfer support 14 by heating and irradiating with an ultraviolet ray. Further, probes prepared by labeling DNA or RNA with fluorescent dye, which is complementary to the DNA containing specific three kinds of genes and the denatured DNA fragments on the transfer support 14 are hybridized by heating to form double-stranded DNA fragments or combined DNA and RNA. Since this embodiment is intended to detect three kinds of DNAs, three kinds of fluorescent dyes releasing fluorescent light having different wavelength from each other, for example, Fluorescein, Rhodamine B and Cy-5, are used for labeling DNAs or RNAs complementary to each of DNAs containing a specific gene to prepare the probes. Since the denatured DNA fragments are fixed on the transfer support 14 at this time, only DNA fragments which are complementary to the probe DNA or probe RNA are hybridized to acquire the fluorescently labeled probe. Then, the probes which have not formed hybrids are removed by washing with a proper solution and only the DNA fragments having a specific gene form hybrids with the fluorescently labeled DNA or RNA on the transfer support 14 to be fluorescently labeled. The thus obtained transfer support 14 records an electrophoresis image of denatured DNAs labeled with fluorescent dyes.

Figure 2:
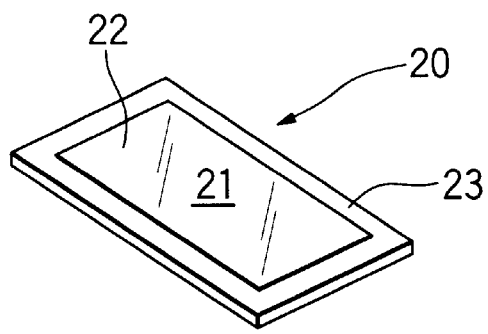
FIG. 2 is a schematic perspective view showing a stimulable phosphor sheet unit.

When a radiation image or an electron image of the object recorded in a stimulable phosphor layer formed on a stimulable phosphor sheet is read out, instead of the fluorescent image carrier unit 12, a stimulable phosphor sheet unit 20 is set in the image reading apparatus. As shown in FIG. 2, the stimulable phosphor sheet unit 20 includes a stimulable phosphor sheet 22 formed with a stimulable phosphor layer 21 on one surface thereof and a magnetic layer (not shown) on the other surface thereof and a support plate 23 such as an aluminum plate onto which gum-like magnetic sheet (not shown) is adhered on one surface thereof. The magnetic layer of the stimulable phosphor sheet 22 and the magnetic sheet of the support plate 23 are adhered by magnetic force and integrated.

The stimulable phosphor layer 21 formed on the stimulable phosphor sheet 22 records, for example, locational information regarding a radioactivity labeled substance contained in a gene produced by Southern blot hybridization method. Locational information as termed here indicates a variety of information relating to the location of radioactively labeled substances, or aggregations thereof, present in a specimen, such as the location, the shape, the concentration, the distribution or combination thereof.

The locational information regarding a radioactively labeled substance is stored in the stimulable phosphor layer 21 of the stimulable phosphor sheet 22, for example, in the following manner. First, a plurality of DNA fragments containing a specific gene are separated and distributed on a gel support by means of electrophoresis and are denatured by alkali processing to form single-stranded DNA. Then, according to the known Southern blotting method, the gel support and a transfer support such as a nitrocellulose filter are placed in layers to transfer at least a part of the denatured DNA onto the transfer support and the transferred DNA fragments are fixed on the transfer support by heating and UV radiation. Further, probes prepared by radioactively labeling DNA or RNA which is complementary to the DNA containing a target gene and the denatured DNA fragments are hybridized by heating to form double-stranded DNA fragments or combined DNA and RNA. Since the denatured DNA fragments are fixed on the transfer support at this time, only the DNA fragments which are complementary to the probe DNA or probe RNA are hybridized to acquire the radioactively labeled probe. Then, the probes which have not formed hybrids are removed by washing with proper solution and only the DNA fragments having a target gene form the hybrids with the radioactively labeled DNA or RNA on the transfer support to be radioactively labeled. The transfer support thus produced and the stimulable phosphor sheet 22 are stacked for a certain period of time to expose the stimulable phosphor layer 21 and at least a part of the radiation emitted from the radioactively labeled substance on the transfer support is absorbed in the stimulable phosphor layer 21 formed on the stimulable phosphor sheet 22, whereby the positional information regarding the radioactively labeled substance in the specimen is stored in the form of an image in the stimulable phosphor layer 21.

Figure 3:
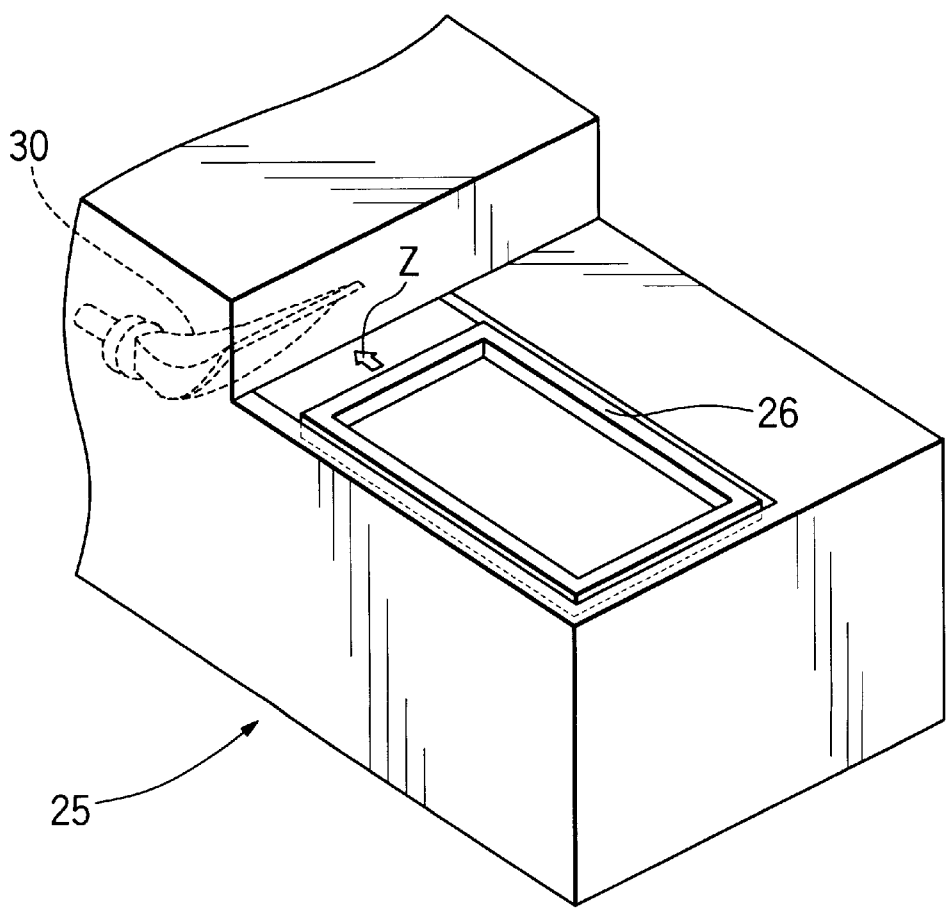
FIG. 3 is a schematic perspective view showing the exterior of an image reading apparatus which is the first embodiment of the present invention.

FIG. 3 is a schematic perspective view showing the exterior of an image reading apparatus which is an embodiment of the present invention.

As shown in FIG. 3, the image reading apparatus 25 includes a sample stage 26 on which the image carrier unit 12 or the stimulable phosphor sheet unit 20 is set. The image carrier unit 12 or the stimulable phosphor sheet unit 20 set on the sample stage is conveyed by a conveyance mechanism (not shown) in the direction indicated by Z in FIG. 3 and is located at a predetermined position in the image reading apparatus 25 to be scanned with the laser beam 4.

The image carrier unit 12 or the stimulable phosphor sheet unit 20 is conveyed by a motor (not show) in the direction of the arrow Y, namely, the sub-scanning direction in FIG. 1 in synchronism with the scanning with the laser beam 4 in the main scanning direction so that the whole surface of the transfer support 14 or the stimulable phosphor layer 21 in the stimulable phosphor sheet 22 is scanned by the laser beam 4.

Upon being irradiated with the laser beam 4, the fluorescent dye contained in the transfer support 14 or the stimulable phosphor contained in the stimulable phosphor layer 21 formed on the stimulable phosphor sheet 22 is excited and releases fluorescent light or stimulated emission. The fluorescent light or the stimulated emission thus released enters a light guide 30 closely positioned so as to face the scanning line of the transfer support 14 or the stimulable phosphor sheet 22.

The light receiving end of the light guide 30 has a linear shape and the exit end thereof is disposed close to a light receiving surface of a light detector 31 for photoelectrically detecting light. This light guide 30 is made by processing non-fluorescent glass or the like and so constructed that fluorescent light introduced from the light receiving end is transmitted to the exit end under repeated total reflection within the light guide 30 and received by the light receiving surface of the light detector 31 via the exit end.

Therefore, during scanning with the laser beam 4, the fluorescent light emitted from the fluorescent dye contained in the transfer support 14 or the stimulated emission released from the stimulable phosphor layer 21 formed on the stimulable phosphor sheet 22 enters the light guide 30 and is received by the light detector 31 via the exit end under repeated total reflection within the light guide 30.

Figure 4:
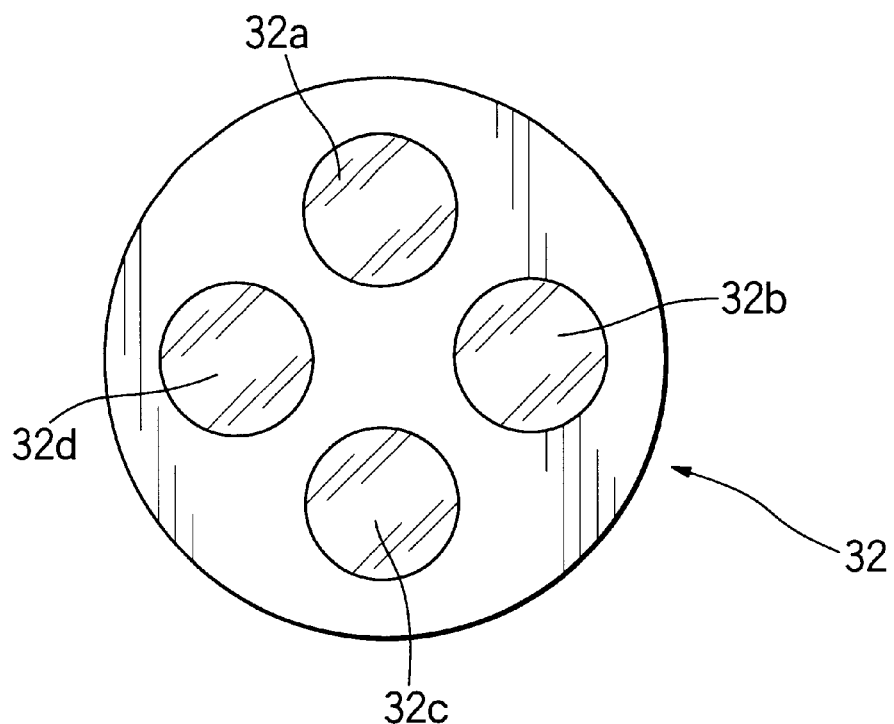
FIG. 4 is a schematic front view showing a filter member.
Figure 5:
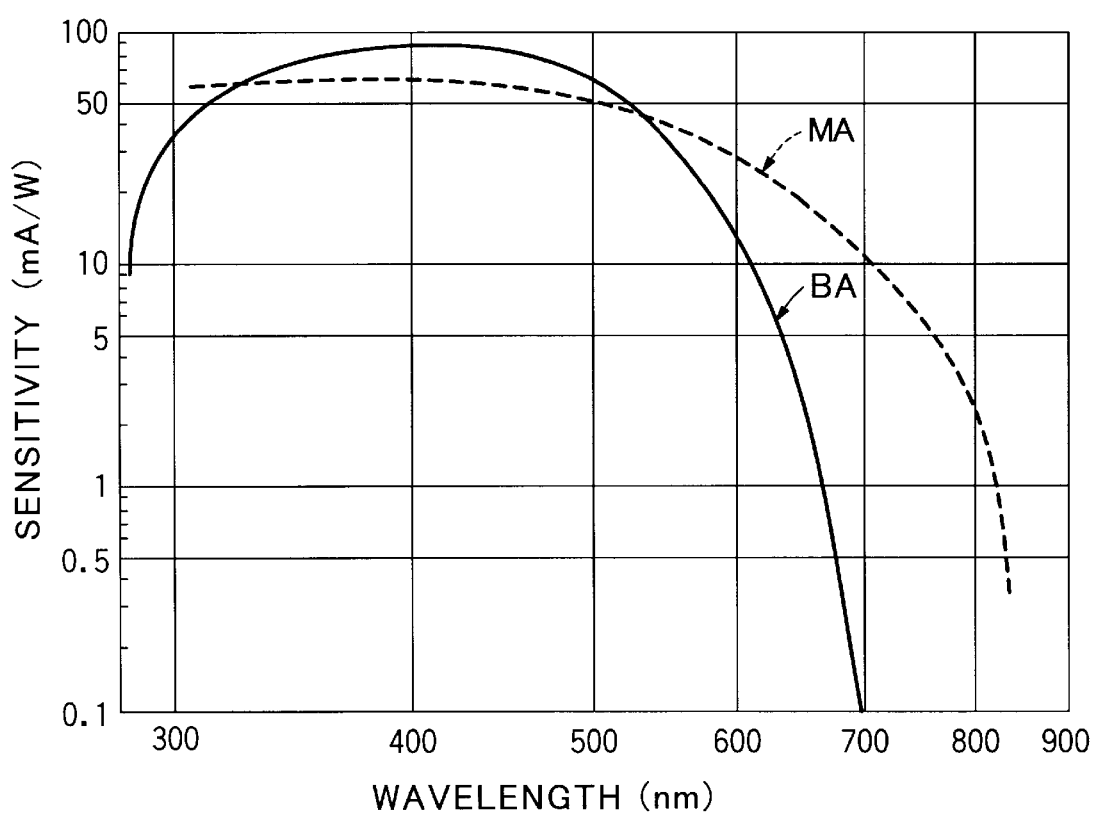
FIG. 5 is a diagram showing sensitivity characteristics of the photomultiplier used in the first embodiment.

In front of the light receiving surface of the light detector 31 is provided a filter member 32. FIG. 4 is a schematic front view of the filter member 32. The filter member 32 is constituted by rotatable disk provided with four filters 32a, 32b, 32c and 32d. The filter 32a is used for reading fluorescent light released from the fluorescent dye contained in the transfer support 14 upon being excited using the first laser stimulating ray source 1 and has a property of cutting off light having a wavelength of 633 nm but transmitting light having a wavelength longer than 633 nm. The filter 32b is used for reading fluorescent light released from the fluorescent dye contained in the transfer support 14 upon being excited using the second laser stimulating ray source 2 and has a property of cutting off light having a wavelength of 532 nm but transmitting light having a wavelength longer than 532 nm. The filter 32c is used for reading fluorescent light released from the fluorescent dye contained in the transfer support 14 upon being excited using the third laser stimulating ray source 3 and has a property of cutting off light having a wavelength of 473 nm but transmitting light having a wavelength longer than 473 nm. The filter 32d is used for reading stimulated emission released from the stimulable phosphor sheet when the stimulable phosphor contained in the stimulable phosphor layer formed on the stimulable phosphor sheet is excited using the first laser stimulating ray source 1 and has a property of allowing only light of a wavelength region of the stimulated emission released from the stimulable phosphor to pass through and cutting off light having a wavelength of 633 nm. Therefore, in accordance with the laser stimulating ray source to be employed, namely, the kind of fluorescent dye and the kind of the image carrier, in other words, whether the image carrier is a stimulable phosphor sheet or not, the light detector can be operated to photoelectrically detect only light to be detected by selectively employing the filters 32a, 32b, 32c and 32d. The filter member 32 can be rotated by a motor 33. A photomultiplier containing a bialkali material based on the compound $K_2CsSb$ prepared by activation with oxygen and cesium is used as the light detector 31. FIG. 5 is a diagram showing sensitivity characteristics of the photomultiplier containing a bialkali material and used in the first embodiment and a photomultiplier containing a multi-alkali material based on the compound $Na_2KSb$ prepared by activation with a small amount of cesium. As shown in FIG. 5, a photomultiplier containing multi-alkali material whose sensitivity curve is indicated by MA has high sensitivity also in a wavelength range longer than 700 nm. On the other hand, a photomultiplier containing bialkali material whose sensitivity curve is indicated by BA is essentially sensitive to light having wavelength equal to and shorter than 700 nm and has significantly low sensitivity with respect to a light having wavelength longer than 700 nm.

In this embodiment, each of the filters 32a, 32b, 32c used for reading the fluorescent image from fluorescent dye contained in the transfer 14 support upon being excited, is made of material which emits fluorescent light whose peak wavelength is longer than 700 nm and longer than 633 nm, 532 nm and 473 nm by at least 80 nm when excited by a laser beam. Specifically, a "2-64" filter (available from Corning International Co.) is used as the filter 32a and this filter emits the fluorescent light having peak wavelength at approximately 740 nm upon receiving laser beam 4 from the first laser stimulating ray source 1. A "2-73" filter (available from Corning International Co.) is used as the filter 32b and this filter emits fluorescent light having a peak wavelength at approximately 740 nm upon receiving the laser beam 4 from the second laser stimulating ray source 2. A "3-69" filter (available from Corning International Co.) is used as the filter 32c and this filter emits fluorescent light having a peak wavelength at approximately 710 nm upon receiving the laser beam 4 from the third laser stimulating ray source 3.

The light photoelectrically detected by the light detector 31 is converted to an electrical signal, amplified by an amplifier 34 having a predetermined amplifying factor so as to produce an electrical signal of a predetermined level and then input to an A/D converter 35. The electrical signal is converted in the A/D converter 35 to a digital signal with a scale factor suitable for the signal fluctuation width and input to a line buffer 36. The line buffer 36 temporarily stores image data corresponding to one scanning line. When the image data corresponding to one scanning line have been stored in the line buffer 36 in the above described manner, the line buffer 36 outputs the data to a transmitting buffer 37 whose capacity is greater than that of the line buffer 36 and when the transmitting buffer 37 has stored a predetermined amount of image data, it outputs the image data to an image processing apparatus 38. The image data input to the image processing apparatus 38 are stored in an image data storing means (not shown). The image data are read out from the image data storing means, image-processed as occasion demands and displayed on display means such as a CRT (not shown) as a visual image or analyzed by an image analyzing apparatus (not shown).

The image reading apparatus according to this embodiment further includes a control unit 40 and input means 41 including a keyboard and the like. A memory (not shown) provided in the control unit 40 stores information regarding the stimulating ray sources 1,2 or 3 to be used and filters 32a, 32b or 32c to be selected depending on the kind of fluorescent dye. Further, the memory stores an instruction that the first laser stimulating ray source 1 is to be used and the filter laser 32d is selected when an image recorded in the stimulable phosphor layer 21 formed on the stimulable phosphor sheet 22 is to be read out. Therefore, when reading of a fluorescent image recorded in the transfer support 14 is to be performed, the operator inputs the kind of the fluorescent dye contained in the transfer support 14 to the input means 41. On the other hand, when the reading of a radiation image recorded in the stimulable phosphor layer 21 formed on the stimulable phosphor sheet 22 is to be performed, the operator inputs that image carrier is a stimulable phosphor sheet to the input means 41. In response to such input by the operator, one of the first, second and third laser stimulating ray sources 1, 2 and 3 to be used and one of the filter 32a, 32b, 32c and 32d to be used are automatically selected by the control unit 40 and the image reading is started. That is, when the kind of the fluorescent dye is input via the input means 41, motor 33 is driven to rotate the filter member 32 and to position one of the filters 32a, 32b or 32c corresponding to the kind of the fluorescent dye contained in the transfer support 14 in front of the light detector 31 and one of the laser stimulating ray source 1, 2 or 3 is selectively driven to radiate the laser beam 4 by the control unit 40 for starting image reading. On the other hand, when the operator inputs that the image carrier is a stimulable phosphor sheet to the input means 41, the control unit 40 drives the motor 33 to rotate the filter member 32 SO as to position the filter 32d in front of the light detector 31 and activates the first laser stimulating ray source 1 to emit the laser beam 4 for starting the image reading.

When the electrophoresis image of denatured DNAs labeled with fluorescent dye contained in the transfer support 14 is read, the image carrier unit 12 is set on the sample stage in the image reading apparatus 25 to be moved to the position shown in FIG. 1 and the kind of the fluorescent dye used for labeling the probe is input through the input means 41 by the operator. The image reading apparatus of this embodiment includes the first laser stimulating ray source 1 for emitting a laser beam having a wavelength of 633 nm, the second laser stimulating ray source 2 for emitting a laser beam having a wavelength of 532 nm and the third laser stimulating ray source 3 for emitting a laser beam having a wavelength of 473 nm, and in this embodiment DNA fragments of the target gene are labeled with three kinds of fluorescent dye, namely, Fluorescein, Rhodamine B and Cy-5, respectively. The wavelength of the light capable of most efficiently stimulating Fluorescein is 490 nm, the wavelength of light capable of most efficiently stimulating Rhodamine B is 534 nm and the wavelength of light capable of most efficiently stimulating the fluorescent dye Cy-5 is 650 nm. Therefore, it is efficient to scan the transfer support 14 using the third laser stimulating ray source 3 for detecting the DNA labeled with Fluorescein, to scan the transfer support 14 using the second laser ray 2 for detecting DNA labeled with Rhodamine B and to scan the transfer support 14 using the first stimulating ray source 1 for detecting the DNA labeled with the fluorescent dye Cy-5.

In view of the above, the image reading apparatus according to this embodiment is adapted so that the user can input and specify through the input means 41 the kind of the fluorescent dye forming a fluorescent image to be read and the sequence of the fluorescent images to be read. When the user inputs an instruction signal through the input means 41 requesting that a fluorescent image of DNA labeled with the fluorescent dye Cy-5 be read first, a fluorescent image of DNA labeled with Rhodamine B be read second and a fluorescent image of DNA labeled with Fluorescein be read last, the control unit 40 first outputs a drive signal to the motor 33 to rotate the filter member 32 50 that the filter 32a is positioned in front of the light receiving surface of the light detector 31, activates the first laser stimulating ray source 1 and turns on the light modulator 15. As a result, a laser beam 4 having a wavelength of 633 nm is emitted from the first laser stimulating ray source 1. The laser beam 4 passes through the light modulator 15 and is transmitted through the dichroic mirrors 6,7 and the beam diameter thereof is accurately adjusted by the beam expander 8. The laser beam 4 impinges upon the polygon mirror 9. The beam deflected by the polygon mirror 9 passes through the fΘ lens 10 and is reflected by the mirror 11. The laser beam 4 reflected by the mirror 11 impinges onto the transfer support 14. Since the laser beam 4 is scanned on the surface of the transfer support 14 in the main scanning direction indicated by X in FIG. 1, while the image carrier unit 12 is moved in the sub-scanning direction indicated by Y in FIG. 1, the whole surface of the transfer support 14 is scanned with the laser beam 4 having a wavelength of 633 nm. As a result, the fluorescent dye Cy-5 contained in the transfer support 14 is excited and releases fluorescent light having a peak wavelength of 667 nm.

The fluorescent light released from Cy-5, the fluorescent dye contained in the transfer support 14, is introduced into the light guide 30 and transmitted to the exit end under repeated total reflection within the light guide 30 and impinges on the filter 32a. Since the filter 32a cuts a light having a wavelength of 633 nm, which corresponds to the wavelength of the stimulating ray, and transmits light having a wavelength longer than 633 nm and the wavelength of the fluorescent light released from the fluorescent dye is longer than the wavelength of the stimulating ray, only fluorescent light released from the fluorescent dye Cy-5 is introduced into and photoelectrically detected by the light detector 31. Since a part of the laser beam 4 emitted from the first stimulating ray source 1 is reflected in the apparatus and impinges onto the filter 32a to excite the filter, the filter 32a releases fluorescent light. However, the filter 32a is made of a material which emits fluorescent light whose peak wavelength is approximately 740 nm and longer than 633 nm by more than 80 nm when excited by the laser beam having wavelength of 633 nm and the light detector 31 is essentially sensitive to a light having wavelength shorter than 700 nm. Therefore, even if the fluorescent light released from the excited filter 32a is received by the light detector 31, it does not produce noise in the resultant image. The image signal produced from the photoelectrically detected fluorescent light is amplified by the amplifier 34 to an electrical signal having a predetermined level. The electrical signal is then converted by the A/D converter 35 to a digital signal with a scale factor suitable for the signal function width and is stored in the line buffer 36. When the image data corresponding to one scanning line have been stored in the line buffer, the line buffer 36 outputs the data to the transmitting buffer 37.

The image data obtained by detecting the fluorescent light released from the fluorescent dye Cy-5 are output from the transmitting buffer 37 to the image processing apparatus 38 and displayed on a display means such as a CRT display as a visible image. The displayed image includes an image of DNA labeled with fluorescent dye Cy-5 and the image data produced in the above described manner are stored in an image storing means (not shown) or are analyzed by an image analyzing apparatus (not shown) as occasion demands.

When the excitation of fluorescent dye by the first stimulating ray source 1 has been completed, the control unit turns off the light modulator 15 to cut the laser beam 4 emitted from the first laser stimulating ray source 1 and outputs a drive signal to a motor (not shown) to return the image carrier unit 12 to its original position. The control unit 40 then outputs a drive signal to the motor 33 to rotate the filter member 32 so that the filter 32b is positioned in front of the light receiving surface of the light detector 31 and activates the second laser stimulating ray source 2. As a result, a laser beam 4 having a wavelength of 532 nm is emitted from the second laser stimulating ray source 2, reflected by the dichroic mirror 6 and passes through the dichroic mirror 7. After the beam diameter of the laser beam 4 is accurately adjusted by the beam expander 8, the laser beam 4 impinges on the polygon mirror 9. The laser beam 4 deflected by the polygon mirror 9 passes through the fΘ lens 10 and is reflected by the mirror 11 to impinge upon the transfer support 14. Since the laser beam 4 is scanned on the surface of the transfer support 14 in the main scanning direction, while the image carrier unit 12 is moved in the sub-scanning direction, the whole surface of the transfer support 14 is scanned with the laser beam 4 having wavelength of 532 nm. As a result, Rhodamine B contained in the transfer support 14 is excited and releases fluorescent light having a peak wavelength of 605 nm.

The fluorescent light released from the Rhodamine B contained in the transfer support 14 enters the light guide 30 and impinges on the filter 32b via the exit end of the light guide 30 under repeated total reflection within the light guide 30. Since the filter 32b cuts a light having a wavelength of 532 nm, which corresponds to the wavelength of the stimulating ray, but transmits light having a wavelength longer than 532 nm and the wavelength of the fluorescent light released from the fluorescent dye is longer than the wavelength of the stimulating ray, only fluorescent light released from the Rhodamine B is introduced into and photoelectrically detected by the light detector 31. Since a part of the laser beam 4 emitted from the second stimulating ray source 2 is reflected in the apparatus and impinges onto the filter 32b to excite the filter, the filter 32b releases fluorescent light. However, the filter 32b is made of a material which emits fluorescent light whose peak wavelength is approximately 740 nm and longer than 532 nm by more than 80 nm when excited by the laser beam having wavelength of 532 nm and the light detector 31 is essentially sensitive to a light having wavelength shorter than 700 nm. therefore, even if the fluorescent light released from the excited filter 32b is received by the light detector 31, it does not produce noise in the resultant image. The image signal produced from the photoelectrically detected fluorescent light is amplified by the amplifier 34 to an electrical signal having a predetermined level. The electrical signal is then converted by the A/D converter 35 to a digital signal with a scale factor suitable for the signal function width and is stored in the line buffer 36. When the image data corresponding to one scanning line have been stored in the line buffer, the line buffer 36 outputs the data to the transmitting buffer 37.

The image data obtained by detecting the fluorescent light released from the Rhodamine B are output from the transmitting buffer 37 to the image processing apparatus 38 and displayed on a display means such as a CRT display as a visible image. The displayed image includes an image of DNA labeled with Rhodamine B and the image data produced in the above described manner are stored in an image storing means (not shown) or are analyzed by an image analyzing apparatus (not shown) as occasion demands.

When the excitation of fluorescent dye by the second laser stimulating ray source 2 has been completed, the control unit 40 outputs a drive signal to a motor (not shown) to return the image carrier unit 12 to its original position. The control unit 40 then outputs a drive signal to the motor 33 to rotate the filter member 32 so that the filter 32c is positioned in front of the light receiving surface of the light detector 31 and activates the third laser stimulating ray source 3. As a result, a laser beam 4 having wavelength of 473 nm is emitted from the third laser stimulating ray source 3 and reflected by the dichroic mirror 7. After the beam diameter of the laser beam 4 is accurately adjusted by the beam expander 8, the laser beam 4 impinges on the polygon mirror 9. The laser beam 4 deflected by the polygon mirror 9 passes through the fθ lens 10 and is reflected the mirror 11 to impinge upon the transfer support 14. Since the laser beam 4 is scanned on the surface of the transfer support 14 in the main scanning direction, while the image carrier unit 12 is moved in the sub-scanning direction, the whole surface of the transfer support 14 is scanned with the laser beam 4 having wavelength of 473 nm. As a result, Fluorescein contained in the transfer support 14 is excited and releases fluorescent light having a peak wavelength of 530 nm. Since the fluorescent dye is excited using the third laser stimulating ray source 3 for emitting a laser beam having a wavelength of 473 nm in this embodiment, the intensity of the stimulating ray is stronger than in the case of using an LED as a stimulating ray source. Therefore, it is possible to release sufficient intensity of fluorescent light from the fluorescent dye.

The fluorescent light released from the Fluorescein contained in the transfer support 14 enters the light guide 30 and impinges on the filter 32c via the exit end of the light guide 30 under repeated total reflection within the light guide 30. Since the filter 32c cuts a light having a wavelength of 473 nm, which corresponds to the wavelength of the stimulating ray, but transmits light having a wavelength longer than 473 nm and the wavelength of the fluorescent light released from the fluorescent dye is longer than the wavelength of the stimulating ray, only fluorescent light released from the Fluorescein is introduced into and photoelectrically detected by the light detector 31. Since a part of the laser beam 4 emitted from the third stimulating ray source 3 is reflected in the apparatus and impinges onto the filter 32c to excite the filter, the filter 32c releases the fluorescent light. However, the filter 32c is made of a material which emits fluorescent light whose peak wavelength is approximately 710 nm and longer than 473 nm by more than 80 nm when excited by the laser beam having a wavelength of 473 nm and the light detector 31 is essentially sensitive to a light having wavelength shorter than 700 nm. Therefore, even if the fluorescent light released from the excited filter 32c is received by the light detector 31, it does not produce noise in the resultant image. The image signal produced from the photoelectrically detected fluorescent light is amplified by the amplifier 34 to an electrical signal having a predetermined level. The electrical signal is then converted by the A/D converter 35 to a digital signal with a scale factor suitable for the signal function width and is stored in the line buffer 36. When the image data corresponding to one scanning line have been stored in the line buffer, the line buffer 36 outputs the data to a transmitting buffer 37.

The image data obtained by detecting the fluorescent light released from the Fluorescein are output from the transmitting buffer 37 to the image processing apparatus 38 and displayed on a display means such as a CRT display as a visible image. The displayed image includes an image of DNA labeled with Fluorescein and the image data produced in the above described manner are stored in an image storing means (not shown) or are analyzed by an image analyzing apparatus (not shown) as occasion demands.

On the other hand, when an image of locational information regarding a radioactively labeled substance contained in a gene produced by the Southern blot hybridization method and recorded in the stimulable phosphor layer 21 formed on the stimulable phosphor sheet 22 is to be read, the user first sets the stimulable phosphor sheet unit 20 on the sample stage 26 of the image reading apparatus 25 so that the stimulable phosphor layer 21 is downwardly directed and moves it to the position where the image carrier unit 12 is located in FIG. 1. Simultaneously, the user inputs an instruction through the input means 41 indicating that the image carrier is a stimulable phosphor sheet 22. In accordance with the instruction signal input through the input means 41, the control unit 40 outputs a drive signal to the motor 33 to rotate the filter member 32 so that the filter 32d is positioned in front of the light receiving surface of the light detector 31. The control unit 40 activates the first laser stimulating ray source 1 and turns on the light modulator 15. As a result, a laser beam 4 having a wavelength of 633 nm is emitted from the first laser stimulating ray source 1 and passes through the light modulator 15, the dichroic mirrors 6, 7 and after the beam diameter of the laser beam 4 has been accurately adjusted by the beam expander 8, the laser beam 4 impinges on the polygon mirror 9. The laser beam 4 deflected by the polygon mirror 9 passes through the fθ lens 10 and impinges on and is reflected by mirror 11, thereby entering the stimulable phosphor layer 21 formed on the stimulable phosphor sheet 22. Since the laser beam 4 is scanned on the stimulable phosphor layer 21 formed on the stimulable phosphor sheet 22 in the main scanning direction indicated by X in FIG. 1, while the stimulable phosphor sheet unit 20 is moved in sub-scanning direction indicated by Y in FIG. 1, the whole surface of the stimulable phosphor layer 21 formed on the stimulable phosphor sheet 22 is scanned with the laser beam 4.

When the stimulable phosphor layer 21 is scanned with the laser beam 4 having a wavelength of 633 nm in this manner, the stimulable phosphor contained in the stimulable phosphor layer 21 formed on the stimulable phosphor sheet 22 is excited, thereby releasing stimulated emission.

The stimulated emission released from the stimulable phosphor enters the light guide 30 and passes through the filter 32d via the exit end of the light guide 30 under repeated total reflection within the light guide 30. Since the filter 32d allows only light of the wavelength region of the stimulated emission released from the stimulable phosphor to pass through and cuts off light having a wavelength of 633 nm, only the stimulated emission released from the stimulable phosphor is photoelectrically detected by the light detector 31. The electrical signal generated by the light detector 31 is amplified by the amplifier 34 so as to produce an electrical signal of a predetermined level and then converted in the A/D converter 35 to a digital signal with a scale factor for the signal fluctuation width. The digital signal is further forwarded to the image processing apparatus 38 via the line buffer 36 and the transmitting buffer 37. A visual image is displayed on a display means such as a CRT based on image data input to the image processing apparatus 38. The image date thus produced are stored in the image data storing means (not shown) or analyzed by the image analyzing apparatus (not shown) as occasion demands.

In the above described embodiment, a "2-64" filter available from Corning International Co. is employed as the filter 32a which is used when fluorescent dye contained in the transfer support 14 is excited by the first laser stimulating ray source 1 to read fluorescent light and this filter emits the fluorescent light having peak wavelength at approximately 740 nm upon receiving the laser beam 4 from the first laser stimulating ray source 1. Further, a "2-73" filter available from Corning International Co. is employed as the filter 32b which is used when fluorescent dye contained in the transfer support 14 is excited by the second laser stimulating ray source 2 to read fluorescent light and this filter emits the fluorescent light having peak wavelength at approximately 740 nm upon receiving the laser beam 4 from the second laser stimulating ray source 2. Furthermore, a "3-69" filter available from Corning International Co. is employed as the filter 32c which is used when fluorescent dye contained in the transfer support 14 is excited by the third laser stimulating ray source 3 to read fluorescent light and this filter emits the fluorescent light having peak wavelength at approximately 710 nm upon receiving the laser beam 4 from the third laser stimulating ray source 3. A photomultiplier containing bialkali material based on the compound $K_2CsSb$ prepared by activation with oxygen and cesium is used as the light detector 31 and the light detector is sensitive in a range between 200 nm and 700 nm. Therefore, if the stimulating ray reflected in the apparatus impinges into the filter 32a, 32b or 32c to excite it and the fluorescent light is released from the excited filter and received by the light detector 31, such fluorescent light does not produce noise in the resultant image. As a result, it is possible to read the fluorescent image with high sensitivity.

Figure 6:
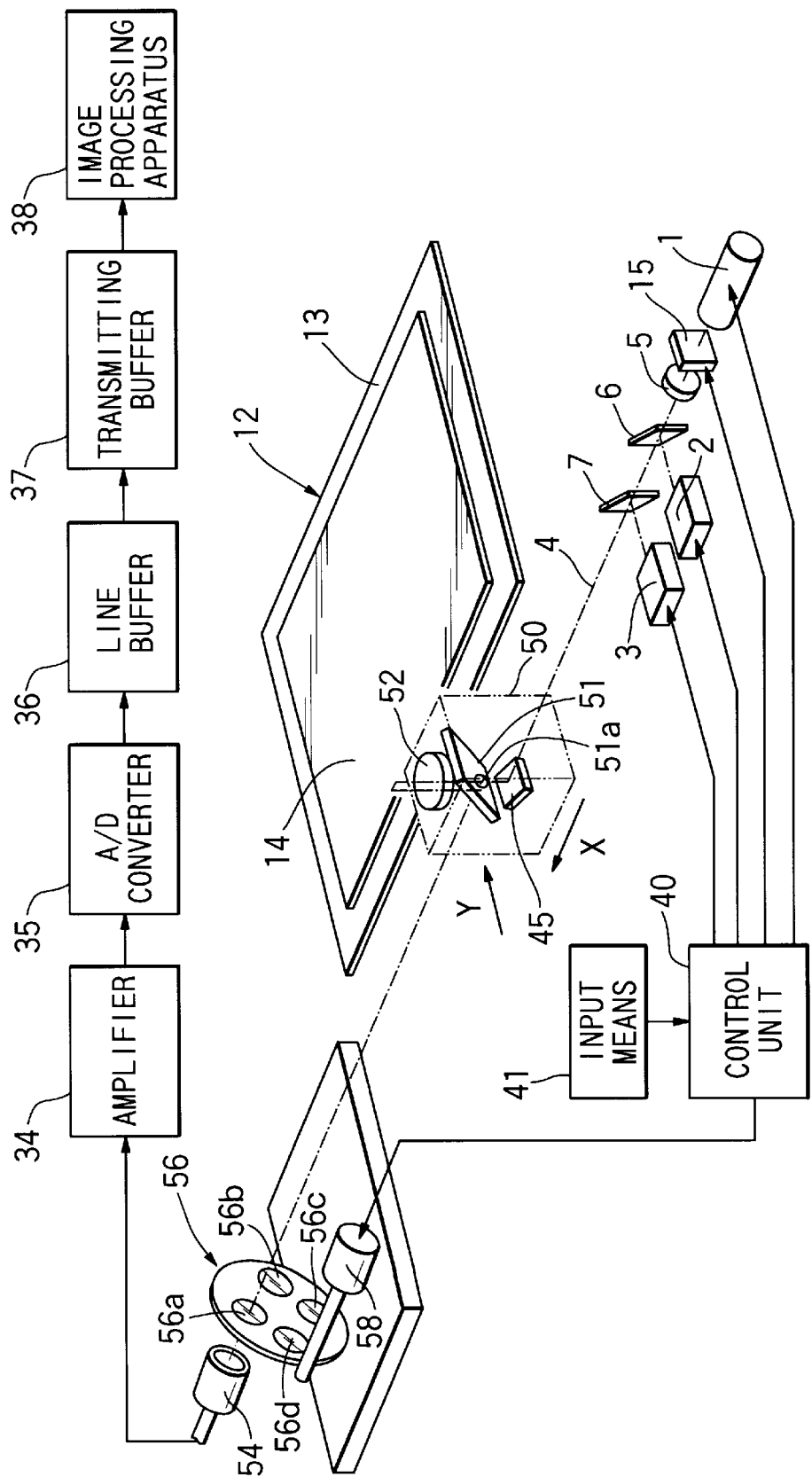
FIG. 6 is a schematic perspective view showing an image reading apparatus which is a second embodiment of the present invention.

FIG. 6 is a schematic perspective view showing an image reading apparatus according to another embodiment of the present invention.

As shown in FIG. 6, the image reading apparatus according to this embodiment includes the first laser stimulating ray source 1, the second laser stimulating ray source 2, the third laser stimulating ray source 3, the filter 5, the first dichroic mirror 6 and the second dichroic mirror 7 similarly to the image reading apparatus shown in FIGS. 1–4. However, the image reading apparatus according to this embodiment is constituted so that both the fluorescent image carrier unit 12 and the stimulable phosphor sheet unit 30 are kept stationary and the whole surface of the transfer support 14 or the stimulable phosphor layer 21 of the stimulable phosphor sheet 22 can be scanned with a laser beam 4 by moving an optical head 50 provided with a mirror 51 formed with a hole 51a at the center thereof and a convex lens 49 for converging the laser beam 4 onto the image carrier. Therefore, a mirror 45 is employed instead of the polygon mirror 9. Further, the image reading apparatus is constituted so that fluorescent light emitted from the transfer support 14 or stimulated emission released from the stimulable phosphor sheet 22 is reflected by the mirror 51 to the side opposite from the first laser stimulating ray source 1, the second laser stimulating ray source 2 and the third laser stimulating ray source 3 and detected by a photomultiplier 54.

Figure 7:
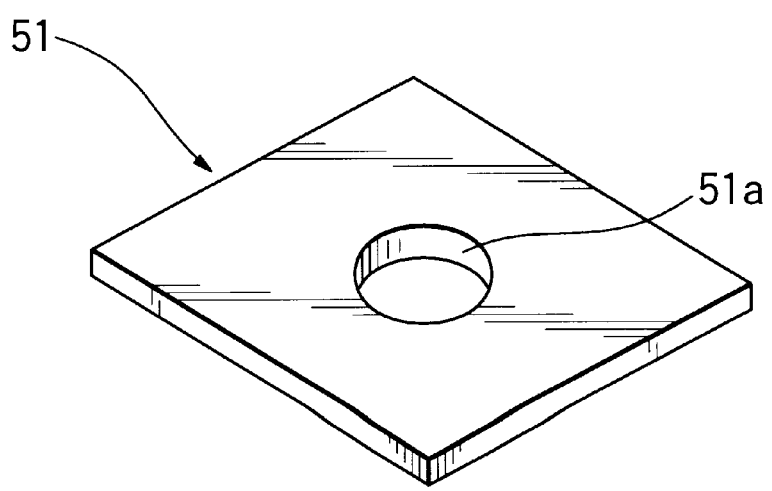
FIG. 7 is a perspective view of a mirror.

FIG. 7 is a schematic perspective view showing the mirror 51. As shown in FIG. 7, the hole 51a is formed at substantially the center of the mirror 51. The diameter of the hole 51a is determined so as to transmit a laser beam emitted from the first laser stimulating ray source 1, the second laser stimulating ray source 2 or the third laser stimulating ray source 3 therethrough but reflect fluorescent light from the transfer support 14 or stimulated emission from the stimulable phosphor sheet 22 as much as possible.

As shown in FIG. 6, the laser beam 4 reflected by the mirror 45 enters the optical head 50 and passes through the hole 51a of the mirror 51. The laser beam 4 is then converged by the convex lens 52 onto the surface of the transfer support 14 or the stimulable phosphor sheet 22, thereby exciting fluorescent dye or the stimulable phosphor. Fluorescent light from the transfer support 14 or stimulated emission from the stimulable phosphor sheet 22 is transformed into a parallel light beam by the convex lens 52 and reflected by the mirror 51 so as to advance to the photomultiplier 54. The photomultiplier 54 contains a bialkali material based on the compound $K_2CsSb$ prepared by activation with oxygen and cesium and can detect light having a wavelength of 200 nm to 700 nm with high sensitivity.

As shown in FIG. 6, a filter member 56 is disposed in front of the photomultiplier 54. The filter member 56 is constituted by a rotatable disk provided with four filters 56a, 56b 56c and 56d. The filter 56a is used for reading fluorescent light released from fluorescent dye contained in the transfer support 14 upon being excited using the first laser stimulating ray source 1 and has a property of cutting off light having a wavelength of 633 nm but transmitting light having a wavelength longer than 633 nm. The filter 56b is used for reading fluorescent light released from fluorescent dye contained in the transfer support 14 upon being excited using the second laser stimulating ray source 2 and has a property of cutting off light having a wavelength of 532 nm but transmitting light having a wavelength longer than 532 nm. The filter 56c is used for reading fluorescent light released from fluorescent dye contained in the transfer support 14 upon being excited using the third laser stimulating ray source 3 and has a property of cutting off light having a wavelength of 473 nm but transmitting light having a wavelength longer than 473 nm. The filter 56d is used for reading stimulated emission released from the stimulable phosphor sheet 22 when the stimulable phosphor contained in the stimulable phosphor layer 21 formed on the stimulable phosphor sheet 22 is excited using the first laser stimulating ray source 1 and has a property of allowing only light of the wavelength region of the stimulated emission released from the stimulable phosphor to pass through and cuts off light having a wavelength of 633 nm. Therefore, in accordance with the laser stimulating ray source to be employed, namely, the kind of fluorescent dye and the kind of image carrier, in other words, whether the image carrier is a stimulable phosphor sheet or not, the light detector 31 can be operated to photoelectrically detect only light to be detected by driving the motor 58 and by selectively employing the filters 56a, 56b, 56c and 56d.

In this embodiment, each of the filters 56a, 56b and 56c used for reading the fluorescent light released from the fluorescent dye contained in the transfer support 14 upon being excited, is made of material which emits fluorescent light whose peak wavelength is longer than 700 nm and longer than 633 nm, 532 nm and 473 nm by at least 80 nm respectively when excited by a laser beam. Specifically, a "2-64" filter (available from Corning International Co.) is used as the filter 56a and this filter emits fluorescent light having peak wavelength at approximately 740 nm upon receiving laser beam 4 from the first laser stimulating ray source 1. A "2-73" filter (available from Corning International Co.) is used as the filter 56b and this filter emits fluorescent light having a peak wavelength at approximately 740 nm upon receiving the laser beam 4 from the second laser stimulating ray source 2. A "3-69" filter (available from Corning International Co.) is used as the filter 56c and this filter emits fluorescent light having a peak wavelength at approximately 710 nm upon receiving the laser beam 4 from the third laser stimulating ray source 3.

Figure 8:
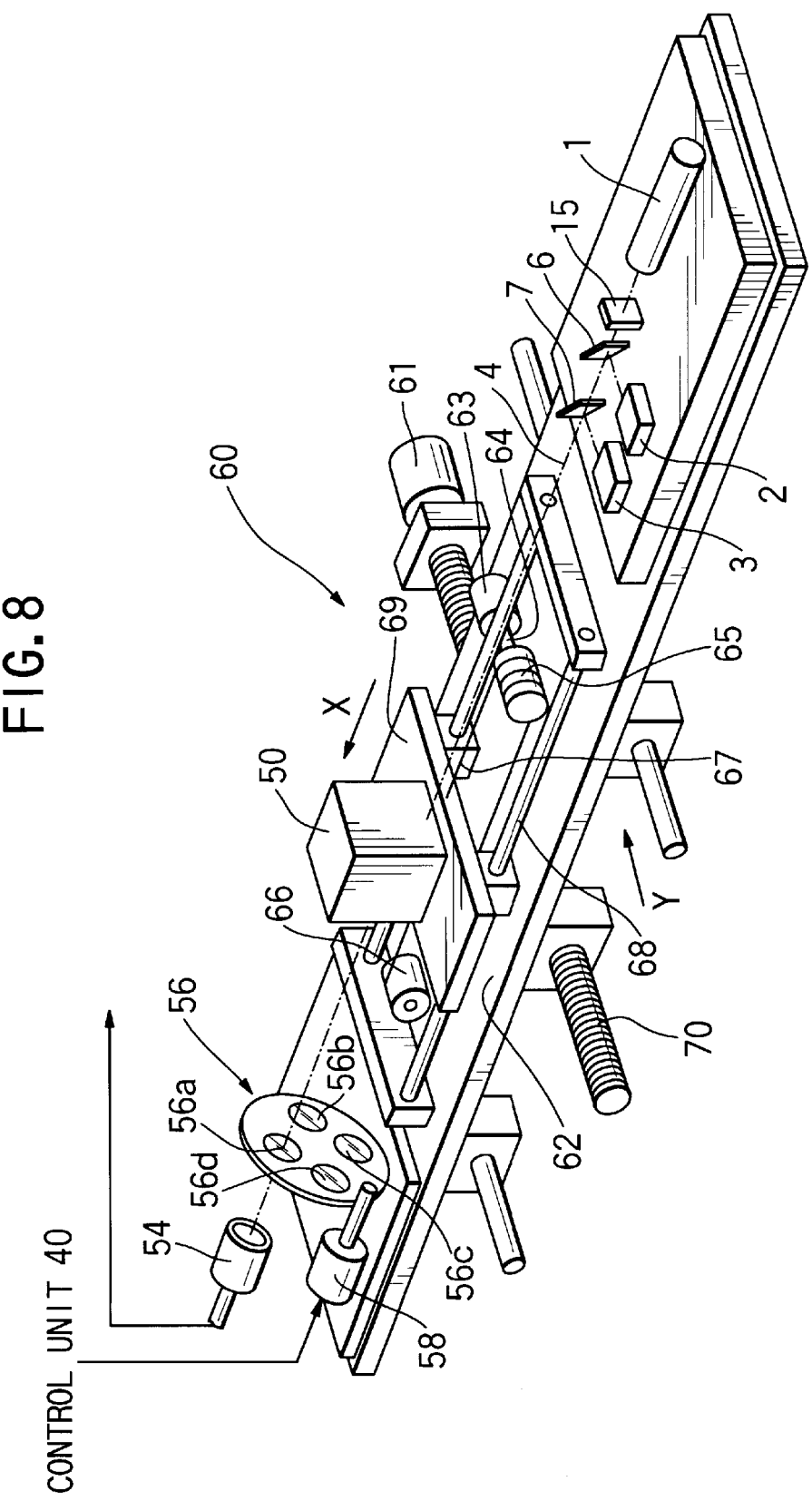
FIG. 8 is a perspective view of an optical unit of the second embodiment of the present invention.

FIG. 8 is a schematic perspective view showing an optical unit provided with the optical head 50.

As shown in FIG. 8, the optical unit 60 includes a bed 62 movable by a sub-scanning motor 61 in a sub-scanning direction indicated by Y in FIG. 8, a main scanning motor 63 fixed on the bed 62, a drive rotating member 65 fixed to an output shaft 64 of the main scanning motor 63, a driven rotating member 66, a wire 67 wound around the drive rotating member 65 and the driven rotating member 66, an optical head stage 69 to which the ends of the wire are fixed and which is movable in a main scanning direction indicated by X in FIG. 8 while being guided by guide rails 68, and the optical head 50 fixed on the optical head stage 69. A threaded rod 70 is fixed to the output shaft (not shown) of the sub-scanning motor 61 and the bed 62 can be moved in the sub-scanning direction as the sub-scanning motor 61 rotates. The photomultiplier 54, the filter member 56, the motor 58 are fixed on the bed 62.

FIG. 6 shows an example in which an image of fluorescent dye recorded in the transfer support 14 is to be read. In the case where the image of fluorescent dye is to be read, the kind of fluorescent dye is input by the user through the input means 41 and in accordance with the input instruction signal, the control unit 40 activates one among the first laser stimulating ray source 1, the second laser stimulating ray source 2 and the third laser stimulating ray source 3. A laser beam 4 emitted from the selected one of the first laser stimulating ray source 1, the second laser stimulating ray source 2 and the third laser stimulating ray source 3 and reflected by the mirror 45 passes through the hole of the mirror 51 and is converged by the convex lens 52 onto the surface of the transfer support 14 on the glass plate 13. As a result, fluorescent dye contained in the transfer support 14 is excited to release fluorescent light.

The fluorescent light released from the fluorescent dye contained in the transfer support 14 is transformed into a parallel light beam by the convex lens 52 and reflected by the mirror 51 in the direction opposite from the first laser stimulating ray source 1, the second laser stimulating ray source 2 and the third laser stimulating ray source 3.

In this embodiment, DNA fragments of the target gene are also labeled with three kinds of fluorescent dye, namely, Fluorescein, Rhodamine B and Cy-5, and a fluorescent image is recorded in the to transfer support 14. When the fluorescent images of DNA fragments of the target gene labeled with Cy-5, Rhodamine B and Fluorescein are read in this order, the user inputs through the input means 41 an instruction requesting that the fluorescent images be sequentially read and the kinds of fluorescent dye sequentially read.

When such instruction signals are input through the input means 41, in accordance with the instruction signals, the control unit 40 outputs a drive signal to the motor 58 to rotate the filter member 56 so that the filter 56a is positioned in front of the light receiving surface of the photomultiplier 54. The control unit 40 then activates the first laser stimulating ray source 1 and turns on the light modulator 15. As a result, a laser beam 4 having a wavelength of 633 nm is emitted from the first laser stimulating ray source 1 and passes through the light modulator 15, the filter 5, and the dichroic mirrors 6, 7. The laser beam 4 is then reflected by the mirror 45 and enters the optical head 50. The laser beam 4 entering the optical head 50 passes through the hole 51a of the mirror 51 and is converged by the convex lens 52 onto the transfer support 14. Since the optical head 50 is moved by the main scanning motor 63 in the main scanning direction indicated by X in FIGS. 6 and 8, while the bed 62 on which the optical head 50 is mounted is moved by the sub-scanning motor 61 in the sub-scanning direction indicated by Y in FIGS. 6 and 8, the whole surface of the transfer support 14 is scanned with the laser beam 4 having a wavelength of 633 nm. As a result, fluorescent dye Cy-5 contained in the transfer support 14 is excited to release fluorescent light having a peak wavelength at 667 nm.

The fluorescent light released from fluorescent dye Cy-5 contained in the transfer support 14 is reflected by the mirror 51 and photoelectrically detected by the photomultiplier 54. The filter member 56 has been rotated so that the light reflected by the mirror 51 impinges onto the filter 56a. Therefore, the stimulating ray having a wavelength of 633 nm is cut and only light having a wavelength longer than the stimulating ray is photoelectrically detected by the photomultiplier 54. Since a part of the laser beam 4 emitted from the first stimulating ray source is reflected in the apparatus and impinges onto and excites the filter 56a, the filter 56a releases fluorescent light. However, the filter 56a is made of a material which emits fluorescent light whose peak wavelength is approximately 740 nm and longer than 633 nm by more than 80 nm when excited by the laser beam having a wavelength of 633 nm and the photomultiplier 54 is essentially sensitive to a light having wavelength between 200 nm and 700 nm. Therefore, even if the fluorescent light released from the excited filter 56a is received by the light detector 31, it does not produce noise in the resultant image.

The image data obtained by detecting the fluorescent light released from the fluorescent dye Cy-5 are output from the transmission buffer 38 to the image processing apparatus 39 and a visual image is displayed on a display means such as a CRT. The thus displayed image contains the image of DNA labeled with the fluorescent dye Cy-5 and the image data produced in this manner are stored in an image data storing means (not shown) or analyzed by an image analyzing apparatus (not shown).

When the excitation by the first laser stimulating ray source 1 has been completed, the control unit 40 turns off the light modulator 15 and cuts the laser beam 4 emitted from the first laser stimulating ray source 1. The control unit 40 outputs a drive signal to the motor (not shown) to return the image carrier unit 12 to its original position. The control unit 40 then outputs a drive signal to the motor 58 to rotate the filter member 56 so that the filter 56b is positioned in front of the light receiving surface of the photomultiplier 54 and activates the second laser stimulating ray source 2. As a result, a laser beam 4 having a wavelength of 532 nm is emitted from the second laser stimulating ray source 2 and is reflected by the dichroic mirror 6. After the laser beam 4 in has passed through the dichroic mirror 7, it is then reflected by the mirror 45 and enters the optical head 50. The laser beam 4 entering the optical head 50 passes through the hole 51a of the mirror 51 and is converged by the convex lens 52 onto the transfer support 14. Since the optical head 50 is moved by the main scanning motor 63 in the main scanning direction indicated by X in FIGS. 6 and 8, while the bed 62 on which the optical head 50 is mounted is moved by the sub-scanning motor 61 in the sub-scanning direction indicated by Y in FIGS. 6 and 8, the whole surface of the transfer support 14 is scanned with the laser beam 4 having a wavelength of 532 nm. As a result, Rhodamine B contained in the transfer support 14 is excited to release fluorescent light having a peak wavelength at 605 nm.

The fluorescent light released from Rhodamine B contained in the transfer support 14 is reflected by the mirror 51 and photoelectrically detected by the photomultiplier 54. The filter member 56 has been rotated so that the light reflected by the mirror 51 impinges onto the filter 56b. Therefore, the stimulating ray having a wavelength of 532 nm is cut and only light having a wavelength longer than the stimulating ray is photoelectrically detected by the photomultiplier 54. Since a part of the laser beam 4 emitted from the first stimulating ray source 2 is reflected in the apparatus and impinges onto and excites the filter 56b, the filter 56b releases fluorescent light. However, the filter 56b is made of a material which emits fluorescent light whose peak wavelength is approximately 740 nm and longer than 532 nm by more than 80 nm when excited by the laser beam having wavelength of 532 nm and the photomultiplier 54 is essentially sensitive to a light having wavelength between 200 nm and 700 nm. Therefore even if the fluorescent light released from the excited filter 56b is detected by the light detector 31, it does not produce noise in the resultant image.

The image data obtained by detecting the fluorescent light released from Rhodamine B are output from the transmitting buffer 38 to the image processing apparatus 39 and a visual image is displayed on a display means such as a CRT. The thus displayed image contains the image of DNA labeled with Rhodamine B and the image data produced in this manner are stored in an image data storing means (not shown) or analyzed by an image analyzing apparatus (not shown).

When the excitation by the second laser stimulating ray source 2 has been completed, the control unit 40 outputs a drive signal to the sub-scanning motor 61 to return the bed 62 to its original position and outputs a drive signal to the main scanning motor 63 to return the optical head 50 to its original position. The control unit 40 then outputs a drive signal to the first motor 58 to rotate the first filter member 56 so that the filter 56c is positioned in front of the light receiving surface of the photomultiplier 54 and activates the third laser stimulating ray source 3. As a result, a laser beam 4 having a wavelength of 473 nm is emitted from the third laser stimulating ray source 3 and is reflected by the dichroic mirror 7. The laser beam 4 is then reflected by the mirror 45 and enters the optical head 50. The laser beam 4 entering the optical head 50 passes through the hole 51a of the mirror 51 and is converged by the convex lens 52 onto the transfer support 14. Since the optical head 50 is moved by the main scanning motor 63 in the main scanning direction indicated by X in FIGS. 6 and 8, while the bed 62 on which the optical head 50 is mounted is moved by the sub-scanning motor 61 in the sub-scanning direction indicated by Y in FIG. 6 and 8, the whole surface of the transfer support 14 is scanned with the laser beam 4 having a wavelength of 473 nm. As a result, Fluorescein contained in the transfer support 14 is excited to release fluorescent light having a peak wavelength at 530 nm. In this embodiment, since the fluorescent dye is stimulated using the second laser stimulating ray source 62 for emitting a laser beam 4 having a wavelength of 473 nm, the strength of the stimulating ray is higher than that emitted from an LED and, therefore, it is possible to generate a sufficiently great amount of fluorescent light from the fluorescent dye.

The fluorescent light released from Fluorescein contained in the transfer support 14 is reflected by the mirror 51 and photoelectrically detected by the photomultiplier 54. Since the filter member 56 has been rotated about the horizontal axis at predetermined angle prior to the activation of the third laser stimulating ray source 3 and retained in that position, the light reflected by the mirror 51 impinges into the filter 56c at an angle from the vertical direction. Therefore, stimulating ray having wavelength of 473 nm is cut and only light having a wavelength longer than the 473 nm is photoelectrically detected by the photomultiplier 54. Since a part of the laser beam 4 emitted from the third stimulating ray source 3 is reflected in the apparatus and impinges into and excites the filter 56c, the filter 56c releases fluorescent light. However, the filter 56c is made of a material which emits fluorescent light whose peak wavelength is approximately 710 nm and longer than 473 nm by more than 80 nm when excited by the laser beam having wavelength of 473 nm and the photomultiplier 54 is essentially sensitive to light having wavelength between 200 nm and 700 nm. Therefore, even if the fluorescent light released from the excited filter 56c is detected by the photomultiplier 54, it does not produce noise in the resultant image.

The image data obtained by detecting the fluorescent light released from Fluorescein are output from the transmitting buffer 38 to the image processing apparatus 39 and a visual image is displayed on a display means such as a CRT. The thus displayed image contains the image of DNA labeled with Fluorescein and the image data produced in this manner are stored in an image data storing means (not shown) or analyzed by an image analyzing apparatus (not shown).

On the other hand, when a radiation image, an autoradiographic image, a radiographic diffraction image or an electron microscopic image of an object recorded in a stimulable phosphor layer 21 of the stimulable phosphor sheet 22 is read out, instead of the fluorescent image carrier unit 12, the stimulable phosphor sheet unit 20 is set in the image reading apparatus 25 and the stimulable phosphor sheet 22 formed with the stimulable phosphor layer 21 recording locational information regarding a radioactively labeled substance contained in a gene produced by the Southern blot hybridization method is scanned with the laser beam 4.

When a radiation image is read from the stimulable phosphor sheet 22 recording locational information regarding a radioactively labeled substance in a specimen, the operator inputs an instruction indicating that the image carrier is a stimulable phosphor sheet 22. As a result, the control unit 40 outputs a drive signal to the first motor 58 to rotate the filter member 56 so that the filter 56d is positioned in front of the light receiving surface of the photomultiplier 54. The control unit 40 then activates the first laser stimulating ray source 1 and turns on the light modulator 15. As a result, a laser beam emitted from the first laser stimulating ray source 1 passes through the light modulator 15 and the hole 51a formed in the mirror 51 of the optical head 50 and is converged by the convex lens 52 onto the surface of the stimulable phosphor layer 21 formed on the stimulable phosphor sheet 22, whereby the surface of the stimulable phosphor layer 21 is scanned with the laser beam 4 having a wavelength of 633 nm, in the same manner as the transfer support 14, and the stimulable phosphor contained in the stimulable phosphor layer 21 is excited by the laser beam 4 to release stimulated emission. The stimulated emission is transformed into a parallel light beam by the convex lens 52 and is reflected by the mirror 51. The stimulated emission is photoelectrically detected by the photomultiplier 54. Since the filter member 56 has been rotated so as to position the filter 56a in front of the light receiving surface of the photomultiplier 54 prior to the activation of the first laser stimulating ray source 1, the light having a wavelength of 633 nm is cut and only light of the wavelength region of the stimulated emission released from the stimulable phosphor is photoelectrically detected by photomultiplier 54.

The image data obtained by detecting the stimulated emission released from the stimulable phosphor contained in the stimulable phosphor layer 21 formed on the stimulable phosphor sheet 22 are output from the transmission buffer 38 to the image processing apparatus 39 and a visual image is displayed on a display means such as a CRT. The thus displayed image contains the image of DNA labeled with the radioactively labeled substance and the image data produced in this manner are stored in an image data storing means (not shown) or analyzed by an image analyzing apparatus (not shown).

In the above described embodiment, a "2-64" filter available from Corning International Co. is employed as the filter 56a which is used when fluorescent dye contained in the transfer support 14 is excited by the first laser stimulating ray source 1 to read fluorescent light and this filter emits the fluorescent light having peak wavelength at approximately 740 nm upon receiving laser beam 4 from the first laser stimulating ray source 1. Further, a "2-73" filter available from Corning International Co. is employed as the filter 56b which is used when fluorescent dye contained in the transfer support 14 is excited by the second laser stimulating ray source 2 to read fluorescent light and this filter emits the fluorescent light having peak wavelength at approximately 740 nm upon receiving laser beam 4 from the second laser stimulating ray source 2. Furthermore, a "3-69" filter available from Corning International Co. is employed as the filter 56c which is used when fluorescent dye contained in the transfer support 14 is excited by the third laser stimulating ray source 3 to read fluorescent light and this filter emits the fluorescent light having peak wavelength at approximately 710 nm upon receiving laser beam 4 from the third laser stimulating ray source 3. A photomultiplier containing a bialkali material based on the compound $K_2CsSb$ prepared by activation with oxygen and cesium is used as the light detector and the light detector is sensitive in a range between 200 nm and 700 nm. Therefore, if the stimulating ray reflected in the apparatus impinges into the filter 56a, 56b or 56c to excite it and the fluorescent light is released from the filter and detected by the photomultiplier 54, such fluorescent light does not produce the noise in the resultant image. As a result, it is possible to read the fluorescent image in high sensitivity.

The present invention is no way limited to the above described embodiment but changes and modifications may be made without departing from the scope of the claimed invention and they are included within the scope of the claimed invention.

For example, in the above described embodiment, a "2-64" filter available from Corning International Co. is used as filters 32a, 56a, a "2-73" filter available from Corning International Co. is used as filters 32b, 56d and a "3-69" filter available from Corning International Co. is used as filters 32c, 56c, respectively. However, the filter 32a, 56a, 32b, 56b, 32c and 56c are not limited to such filters and may be other kinds of filters made of a material which emits fluorescent light whose peak wavelength is longer than 700 nm and longer than the wavelength of the stimulating ray by at least 80 nm when excited by the stimulating ray.

In the above described embodiment, the light detector 31 and the photomultiplier 54 are photomultipliers containing a bialkali material based on the compound $K_2CsSb$ prepared by activation with oxygen and cesium. However, the light detector and photomultiplier are not limited to such photomultiplier and any light detector or photomultiplier which can efficiently detect the light having a wavelength shorter than 700 nm may be used.

Moreover, the image reading apparatuses of the above described embodiments are constituted so as to be able to read a fluorescent dye electrophoresis image recorded in a gel support, transfer support or the like, a radiation image, an autoradiographic image, a radiographic diffraction image or an electron microscopic image of an object. However, it is sufficient for the image reading apparatus of the present invention to be able to read a fluorescent dye image and it is not necessary for it to be able to read a radiation image, an autoradiographic image, a radiographic diffraction image or an electron microscopic image of an object.

Furthermore, in the above described embodiment, the image reading apparatus comprises the second laser stimulating ray source 2 for emitting a laser beam 4 having a wavelength of 532 nm. However, it is not necessary for the image reading apparatus of the present invention to include the second laser stimulating ray source 2.

Further, in the above described embodiment, although a He—Ne laser is used as the first laser stimulating ray source 1 for emitting a laser beam 4 having a wavelength of 633 nm, a semiconductor laser source for emitting a laser beam having a wavelength of 635 nm may be employed instead of the He—Ne laser.

Furthermore, in the above described embodiment, although the laser beam source for emitting a laser beam having a wavelength of 633 nm, the laser beam source for emitting a laser beam having a wavelength of 532 nm and the laser beam source for emitting a laser beam having a wavelength of 473 nm are respectively used as the first laser stimulating ray source 1, the second laser stimulating ray source 2 and the third laser stimulating ray source 3, a laser beam source for emitting a laser beam having a wavelength of 635 nm may be used for the first laser stimulating ray source 1 instead of the laser beam source for emitting a laser beam 4 having a wavelength of 633 nm and a laser beam source for emitting a laser beam having a wavelength of from 530 nm to 540 nm may be used for the second laser stimulating ray source 2 and a laser beam source for emitting a laser beam having a wavelength of from 470 nm to 480 nm may be used for the third laser stimulating ray source 3.

Moreover, in the above described embodiments, although the light guide 30 made by processing a non-fluorescent glass or the like is employed, the light guide 30 is not limited to one made of a non-fluorescent glass but a light guide made by processing synthesized crystal, a transparent sheet such as an acrylic synthetic resin sheet or the like may be used.

Further, in the above described embodiment, when a fluorescent image recorded in the transfer support 14 is to be read, the kind of the fluorescent dye is input through the input means 41 and when a radiation image recorded in the stimulable phosphor layer formed on the stimulable phosphor sheet 22 is to be read, an instruction indicating that the image carrier is a stimulable phosphor sheet is input through the input means 41, whereby the control unit 40 automatically selects one of the laser stimulating ray sources 1, 2 and 3, and one of the filters 32a, 32b, 32c and 32d. Further, in the embodiment shown in FIGS. 6 and 7, the control unit automatically selects one of the laser stimulating ray sources 1, 2 and 3, and one of the filters 56a, 56b, 56c and 56d. However, the kinds of instruction signals for causing the control unit 40 to effect such automatic selection can be arbitrarily determined and it is not necessary to input the kinds fluorescent dye or that the image carrier is a stimulable phosphor sheet.

Moreover, in the embodiment shown in FIGS. 6–8, the laser beam 4 emitted from the first laser stimulating ray source 1, the second laser stimulating ray source 2 and the third laser stimulating ray source 3 pass through the hole 51a in the mirror 51 and are converged by the convex lens 52 onto the surface of the transfer support 14 or the stimulable phosphor layer 21 and fluorescent light released from the transfer support 14 or stimulable emission released from the stimulable phosphor layer 21 is reflected by mirror 51 in the direction opposite from the first laser stimulating ray source 1, the second laser stimulating ray source 2 and the third laser stimulating ray source 3, and photoelectrically detected. However, it is not necessary to form such hole 51a in the mirror 51 and it is sufficient to form a portion for transmitting a laser beam 4 in the mirror 51 by forming a coated portion which can transmit the laser beam 4 instead of the hole 51a or by providing a total reflection coating on the mirror 51 except at a portion through which laser beam 4 passes.

Further, in the above described embodiments, although the image reading apparatus includes the light modulator 15 and it is preferable to provide the light modulator 15 in case where the laser stimulating ray sources have to be frequently switched, for example, in case where the transfer support 14 is scanned using different laser stimulating ray sources every scanning line. However, the light modulator 15 is not absolutely necessary in the case where the laser stimulating ray sources do not have to be frequently switched, for example in case where the whole surface of the transfer support 14 is scanned using one of the first laser stimulating ray source 1, the second laser stimulating ray source 2 and the third laser stimulating ray source 3 and then scanned using another laser stimulating ray source.

According to the present invention, it is possible to provide an image reading apparatus which can read a fluorescent image with high sensitivity.

What is claimed is:

1. An image reading apparatus comprising:
   at least one laser stimulating ray source for emitting a laser beam,
   a light detector for photoelectrically detecting fluorescent light released from an image carrier upon excitation by said laser beam, said light detector being able to detect light having a wavelength shorter than 700 nm with high sensitivity,
   filter means provided in front of said light detector and made of a material able to cut light having the wavelength of said laser beam and that emits a fluorescent light having a peak wavelength equal to or longer than 700 nm upon excitation by said laser stimulating ray.

2. An image reading apparatus in accordance with claim 1, wherein the peak wavelength of said fluorescent light emitted from said filter means is longer than the wavelength of said stimulating ray by at least 80 nm.

3. An image reading apparatus in accordance with claim 1, wherein said light detector comprises a photomultiplier containing bialkali material and detects the light having a wavelength between 200 nm and 700 nm with high sensitivity.

4. An image reading apparatus in accordance with claim 3, wherein said photomultiplier contains a bialkali material based on the compound $K_2CsSb$ prepared by activation with oxygen and cesium.

5. An image reading apparatus in accordance with claim 2, wherein said at least one laser stimulating ray source is a laser stimulating ray source for emitting a laser beam having a wavelength of 633 nm or 635 nm.

6. An image reading apparatus in accordance with claim 1, wherein said at least one laser stimulating ray source is a laser stimulating ray source for emitting a laser beam having a wavelength between 530 nm and 540 nm.

7. An image reading apparatus in accordance with claim 1, wherein said at least one laser stimulating ray source is a laser stimulating ray source for emitting a laser beam having a wavelength between 470 nm and 480 nm.

8. An image reading apparatus comprising;
   laser beam source means for emitting a laser beam,
   laser scanning means for scanning an image carrier carrying a fluorescent image thereon with the laser beam emitted from said laser 10 beam source means,
   a light detector for photoelectrically detecting fluorescent light released from said image carrier upon excitation by said laser beam, said light detector being able to detect light having a wavelength shorter than 700 nm with high sensitivity,
   filter means provided in front of said light detector for cutting the light having the wavelength of said laser beam and made of a material that emits a fluorescent light having a peak wavelength equal to or longer than 700 nm upon excitation by said laser beam.

9. An image reading apparatus in accordance with claim 8, wherein the peak wavelength of said fluorescent light emitted from said filter means is longer than the wavelength of said laser beam by at least 80 nm.

10. An image reading apparatus in accordance with claim 8, wherein said light detector comprises a photomultiplier containing bialkali material and detects light having a wavelength between 200 nm and 700 nm with high sensitivity.

11. An image reading apparatus in accordance with claim 10, wherein said photomultiplier contains a bialkali material based on the compound $K_2CsSb$ prepared by activation with oxygen and cesium.

12. An image reading apparatus in accordance with claim 9, wherein said laser beam source means is a laser stimulating ray source for emitting a laser beam having a wavelength of 633 nm or 635 nm.

13. An image reading apparatus in accordance with claim 8, wherein said laser beam source means is a laser stimulating ray source for emitting a laser beam having a wavelength between 530 nm and 540 nm.

14. An image reading apparatus in accordance with claim 8, wherein said laser beam source means is a laser stimulating ray source for emitting a laser beam having a wavelength between 470nm and 480 nm.

15. An image reading apparatus in accordance with claim 8, wherein said laser beam source means includes a plurality of laser beam sources which emit a plurality of laser beams having different wavelengths from each other, and wherein said filter means includes a plurality of filters, each of which is made of a material cutting one of said plurality of laser beams and emitting a fluorescent light having a peak wavelength equal to or longer than 700 nm by the excitation of one of said plurality of laser beams.

16. An image reading apparatus in accordance with claim 15, wherein the peak wavelength of said fluorescent light is longer than the wavelength of said laser beam by at least 80 nm.

17. An image reading apparatus in accordance with claim 16, wherein said laser beam source means is a laser stimulating ray source for emitting a laser beam having a wavelength of 633 nm or 635 nm.

18. An image reading apparatus in accordance with claim 15, wherein said laser beam source means is a laser stimulating ray source for emitting a laser beam having a wavelength between 530 nm and 540 nm.

19. An image reading apparatus in accordance with claim 15, wherein said laser beam source means is a laser stimulating ray source for emitting a laser beam having a wavelength between 470 nm and 480 nm.

\* \* \* \* \*